United States Patent
Lindner et al.

(10) Patent No.: US 8,841,124 B2
(45) Date of Patent: Sep. 23, 2014

(54) **METHODS FOR PRODUCING HAIR MICROFOLLICLES AND *DE NOVO* PAPILLAE AND THEIR USE FOR IN VITRO TESTS AND IN VIVO IMPLANTATIONS**

(75) Inventors: Gerd Lindner, Berlin (DE); Roland Lauster, Berlin (DE)

(73) Assignee: Technische Universitat Berlin, Berlin (DE)

( * ) Notice: Subject to any disclaimer, the term of this patent is extended or adjusted under 35 U.S.C. 154(b) by 219 days.

(21) Appl. No.: 12/935,172

(22) PCT Filed: Mar. 23, 2009

(86) PCT No.: PCT/EP2009/053363
§ 371 (c)(1),
(2), (4) Date: Dec. 9, 2010

(87) PCT Pub. No.: WO2009/118283
PCT Pub. Date: Oct. 1, 2009

(65) Prior Publication Data
US 2011/0086079 A1    Apr. 14, 2011

(30) Foreign Application Priority Data
Mar. 28, 2008 (EP) .................................... 08153596

(51) Int. Cl.
| C12N 5/00 | (2006.01) |
| C12N 5/02 | (2006.01) |
| A61L 27/38 | (2006.01) |
| A61L 27/60 | (2006.01) |
| C12N 5/071 | (2010.01) |
| A61L 27/36 | (2006.01) |
| A61K 35/12 | (2006.01) |

(52) U.S. Cl.
CPC ......... *A61L 27/3604* (2013.01); *A61L 27/3886* (2013.01); *C12N 2533/54* (2013.01); *A61L 2430/18* (2013.01); *C12N 2502/094* (2013.01); *A61L 27/60* (2013.01); *A61L 27/3804* (2013.01); *C12N 5/0627* (2013.01); *C12N 2502/1323* (2013.01); *C12N 2533/52* (2013.01); *C12N 2502/092* (2013.01); *A61K 35/12* (2013.01); *A61L 27/3869* (2013.01); *C12N 5/0698* (2013.01)
USPC ............................ 435/378; 435/325; 435/383

(58) Field of Classification Search
USPC ......................................... 435/378, 325, 383
See application file for complete search history.

(56) References Cited

U.S. PATENT DOCUMENTS

2005/0233450 A1    10/2005    Goetinck

FOREIGN PATENT DOCUMENTS

| DE | 101 62 814 | 6/2005 |
| WO | WO 2004/113514 | 12/2004 |
| WO | WO 2005/071063 | 8/2005 |
| WO | WO 2005/113747 | 12/2005 |

OTHER PUBLICATIONS

Magerl et al., Exp. Dermatology 11:381-385, 2002.*
Almond-Roesler et al., Arch Dermatol. Res., 289: 698-704, 1997.*

* cited by examiner

*Primary Examiner* — Thaian N Ton
(74) *Attorney, Agent, or Firm* — Enshan Hong; Kent H. Cheng; VLP Law Group LLP (57) ABSTRACT

The present invention relates to a method for producing hair microfollicles comprising the steps of: a) providing de novo-papillae, b) providing other cell populations selected from the group of fibroblasts, keratinocytes and melanocytes, and co-culturing the de novopapillae with at least one other cell population in non-adherent culture vessels. The present invention relates also to methods of producing de novo papillae usable in said method for producing hair microfollicles.

5 Claims, 4 Drawing Sheets

METHODS FOR PRODUCING HAIR MICROFOLLICLES AND *DE NOVO* PAPILLAE AND THEIR USE FOR IN VITRO TESTS AND IN VIVO IMPLANTATIONS

PRIORITY CLAIM

This is a U.S. national stage of application No. PCT/EP2009/053363, filed on Mar. 23, 2009. Priority is claimed on the following application: EP Application No. 08153596.5 Filed on Mar. 28, 2008, the content of which is incorporated here by reference.

FIELD OF THE INVENTION

The present invention relates to a method for producing hair microfollicles by co-culturing the de novo papillae with another cell population of the hair follicle in the ultra-low attachment culture vessels. The invention also relates to a method for producing de novo papillae usable in a method for producing hair microfollicle. Object of the invention are also the hair microfollicles and the de novo papillae produced by the aforementioned methods. The hair microfollicles and/or de novo papillae can be used as implants for treating reduced hair conditions, and for in vitro testing hair-modulating effects or toxic effects of substances.

BACKGROUND OF THE INVENTION

Because of the critical role that hair plays in human non-verbal communication, an affected individual invariably demands help when hair growth diminishes. The ultimate therapy, of course, is to restore or regenerate new, healthy, cycling hair follicles. Until very recently, medicine was unable to offer any valid treatments to these patients. In the late twentieth century, several drugs were marketed that, however modestly and inconsistently, did stimulate hair growth. Examples are minoxidil, finasteride, and latanoprost. The complex timing and myriad gene expression changes required for orchestration of hair follicle development and cycling are likely to preclude a simple pharmaceutical approach to the treatment of advanced alopecia. Consequently, their effects fall short of the ultimate goal to generate new hair follicles in bald scalp. By taking advantage of cell types that know how to form a hair follicle, cell-based therapies will arrive in the clinic sooner than the purely molecular approach.

One approach to hair follicle cell-based therapy would entail removing a small number of hair follicles, isolating competent and/or inductive cells from them, and then expanding those cells ex vivo while maintaining their special ability to generate new hair follicles. Clearly, cell culture conditions that maintain the inductive ability of dermal follicular cells and the competence of hair follicle epithelial cells are necessary before any type of cell-based therapy for alopecia can be developed. As early studies showed that the inductive property of dermal cells wanes with time in vitro, research has focused on maintaining the trichogenic properties of hair follicle cells in culture. Much of the recent progress has resulted from advances in culture methodology for intact hair follicles, and their cellular components. Human hair follicle cells grown in culture include follicular papilla fibroblasts, outer root sheath (ORS) keratinocytes and germinative epidermal cells from the hair matrix (Tobin et al., J. Invest. Dermatology 104(1), 86-88, 1995).

The goal of current bioengineering efforts is to generate or reconstitute fully organized and functional organ systems starting from dissociated cells that have been propagated under defined tissue culture conditions. It has long been recognized that the hair follicle has profound regenerative ability, in that it cycles over the life-time of the individual and reproduces its lower half cycle after cycle. The fibroblasts of the dermal hair papilla and connective tissue sheath are stem cell-like in character and have specific hair growth-inducing properties. The hair follicle reforms itself by means of interactions between competent epithelial stem cells and powerfully inductive dermal cells during its growth cycle. It is possible to reconstitute a complete hair follicle from epithelial and mesenchymal stem cells of hair follicles.

Major challenges that need to be addressed with any type of cell-based treatment for alopecia include the efficiency of hair follicle formation and the choice of cell type, which are summarized by Stenn & Cotsarelis, Curr. Opinion Biotech. 16, 493-497, 2005. For bioengineering the hair follicle, one could start with dermal elements from dissociated follicles with or without competent cells from the follicle or other epithelial sources. The number of dissociated cells would be expanded in culture, and then dermal cells alone, or in combination with competent epithelial cells, re-introduced to the alopecic scalp. Previous studies have shown that starting with correctly placed inducer dermal cells will result in new follicle formation. Moreover, starting with a combination of dissociated, or aggregated, trichogenic epithelial and dermal cells has also proven to be an efficient way of producing new hair follicles.

First attempts at cell-based approaches for treating alopecia are likely to use autologous tissue for bioengineering hair follicles to avoid immune rejection of the donor cells. However, the intriguing possibility that heterologous (allogeneic) hair follicle tissue could be developed for tissue transplantation exists, based on the concept that the hair follicle is an immune-privileged site that does not express MHC (major histocompatibility complex) class I antigens. Nevertheless, the safety testing and regulatory hurdles for this type of approach would require enormous financial resources.

Another possible approach for bioengineering hair follicles involves actually forming hair follicles as mini organs in vitro, and then transplanting the newly generated follicles back to the alopecic scalp. It is known from DE 101 62 814 B4 that a skin and hair equivalent can be produced by providing a pseudodermis or a pseudodermis preparation, as well as pseudopapillae comprising cultivated dermal papilla cells on a suitable carrier or in a suitable matrix, or pseudopapillae precursors comprising cultivated dermal papilla cells on a suitable matrix-forming medium, capable of forming a matrix in situ, and introducing the pseudopapillae or the pseudopapillae precursor into the pseudodermis or pseudodermis preparation. This sort of approach would require a much more complicated cell culture system involving three-dimensional matrices, perhaps embedded with appropriate growth factors, to allow both dermal and epidermal cells to differentiate towards the three-dimensional structure of a normal hair follicle. Particularly, the papilla structure is only obtained by forming cavities, such as by punching or pricking, in said pseudodermis, and placing said pseudopapillae therein, which are so shaped that their dimensions correspond to the cavities formed in the PD. The approach lacks the voluntary arrangement of cells in the approximate physiological papilla structure, as well as direct cell contacts.

It has been recently shown another method for producing a population of multipotent stem cells or progeny thereof, which are originated from a hair follicle or a dermal papilla-containing portion thereof. The method of WO 2005/071063 A1 comprises the culture of said hair follicle or dermal papilla-containing portion in conditions under which multipotent stem cells grow and proliferate non-adherently. Dermal papillae are not obtained by this procedure, but the isolated multipotent stem cells directly used for inducing hair growth or regenerating skin in a mammal. However, it is also recognized in this document that a certain amount of adherent cells is formed as confirmed in WO 2005/113747 A2, which discloses a method for producing multicellular aggregates from at least two multipotent or pluripotent adult stem cell types by cultivation under steric conditions. Presently, the organoid bodies are restricted to the aforementioned stem cells gathered from exocrine gland tissue.

SUMMARY OF THE INVENTION

Therefore, the technical problem forming the basis of the present invention is to avoid the above-mentioned disadvantages of the prior art and to provide a method for generating re-constructed hair follicle and papillae that arrange free and easy into the size and shape of a physiological DP. Another problem addressed by the present invention is to find a hair equivalent or skin substitute, which would be suitable as an in vitro model, more particularly for testing and/or evaluating active substances, most particularly on the hair follicle.

The present invention solves the problem by providing a method for producing mammalian hair microfollicle comprising the steps of:
(a) providing at least one de novo papilla,
(b) providing at least one other cell population selected from the group of fibroblasts, keratinocytes and melanocytes, and
(c) co-culturing the de novo papilla with the at least one other cell population under non-adherent culture conditions.

The terms "de novo papillae" or "neopapillae" are interchangeably used herein, and denote cell aggregates of mammalian dermal hair papilla fibroblasts (DPF), which have at least half the size and approximately the shape of a physiological dermal papilla (DP) of a hair follicle after isolation. De novo papillae can comprise a coating comprising one or multiple different extracellular matrix proteins, preferably collagen IV, fibronectin and/or laminin. Such coating can be generated by the DPFs forming the de novo papilla themselves, or can be added at any stage before de novo papillae will be co-cultured according to step (c) of the method for producing hair microfollicles.

The terms "microfollicle" and "neofollicle" are used interchangeably herein and refer to an incomplete mammalian hair follicle structure that is composed of the dermal cellular scaffold, but lacking other cell types, such as muscle cells, nerves, blood vessels, etc., resulting in a reduced size if compared to the natural follicle. A microfollicle of the present invention is composed of a de novo papilla that is stably covered or colonized by cells of at least one other cell population selected from the group of fibroblasts, keratinocytes and/or melanocytes. The fibroblasts, keratinocytes and/or melanocytes do not have to originate from a mammalian hair follicle, but can be derived from other mammalian tissues. Preferably a microfollicle of the present invention is composed of a de novo papilla that is stably covered or colonized by cells of at least one other cell population, which is derivable and/or derived from a mammal hair follicle, e.g. selected from the group of fibroblasts of the connective tissue sheath, keratinocytes and/or melanocytes. The three-dimensional form of said microfollicle mimics the three-dimensional appearance of a physiological mammal hair follicle. The microfollicles can in particular be three-dimensionally formed, optionally spatially demarcated, reconstructed de novo papillae with follicle-like structures on the surface of the de novo papillae, including those reminiscent of the earliest stage of hair morphogenesis, and comprising dermal papilla cells.

The invention relates to a method for producing hair microfollicles, comprising multiple steps.

These steps comprise the provision of de novo papillae. According to the invention, the de novo papillae to be provided can be produced by any suitable method, preferably de novo papillae are used that have been produced according to one of the methods for production of de novo papillae according to the invention disclosed below.

The steps comprise further the provision of other cell populations. The other cell population may be derivable from a mammal hair follicle, preferably from the same hair follicle as used for DP preparation, and co-culturing the de novo papillae with at least one other cell population in non-adherent culture vessels. At least 4 different cell populations, i.e. DPFs, fibroblasts of the connective tissue sheath (CTSF), keratinocytes (KC), and melanocytes (MC), can be isolated from a mammal hair follicle in a defined manner, separately cultured under standard conditions, and subsequently multiplied. It is also possible to form cell cultures with long-term viability from these isolates and put them to use, e.g. for screening methods.

It is a preferred embodiment of the present invention that the other cell populations are selected from the group of fibroblasts, keratinocytes, and melanocytes. The fibroblasts, keratinocytes and/or melanocytes do not have to originate from a mammalian hair follicle, but can be derived from other mammalian tissues. The fibroblasts originate preferably from connective tissue sheath.

Preferably the at least one other cell population is derivable and/or derived from a mammal hair follicle, which is selected from the group of fibroblasts of the connective tissue sheath, keratinocytes and/or melanocytes.

It is another preferred embodiment of the present invention that the de novo papillae are co-cultured with keratinocytes at least. Keratinocytes are supplemented for basic microfollicle neogenesis. It is still another preferred embodiment of the invention that keratinocytes and melanocytes are simultaneously provided to the papilla culture. The addition of melanocytes is especially useful for investigations of hair pigmentation, or for the purpose of future implantation with a desired hair color. The other, separately expanded cell components can be added to a non-adherent cell culture vessel described below for the method of producing de novo papillae, such as the ultra-low attachment culture vessels, in which the neopapillae have already been produced. Keratinocytes, or mixtures of keratinocytes and melanocytes are added to the coated neopapillae at a specific mixing ratio and incubated with a suitable medium in the non-adherent culture vessels for several days. Preferable ratios are KC to MC 2:1, 5:1, 10:1 or 20:1. The co-culturing lasts at least 12 hours, preferably between 1 day to 5 weeks, more preferably 2 days to 3 weeks, most preferably 1 week or substantially 2 days. To elaborate a multilayered neofollicle, which even better mimics the hair follicle structure and function, it can be obtained by coating the generated neofollicle with CTSF for a defined period of time selected from 12 hours to 10 days, preferably 1 to 5 days, most preferably substantially 2 days. Under these conditions, the cell mixture develops into a follicular structure, forming hair follicle-typical features, such as development of a hair shaft. The organ-like structure is referred to as microfollicle from the formation of an approximate hair shaft on.

In a preferred embodiment of the method of the invention for producing hair microfollicle
(a) de novo papillae are provided;
(b) de-novo papillae are contacted with KC, MC or a mixture of KC and MC with a predetermined ratio and co-cultured in a non-adherent culture vessel for a predetermined amount of time;
(b') optionally, repeat step (b), preferably wherein cells of a different cell-type are used for contacting and co-culturing than used in the first round;
(c) optionally covered de-novo papillae of step (b) or (b') can be coated with an extracellular matrix protein, preferably collagen IV, prior to and/or simultaneously with step (d);
(d) covered de-novo papillae of step (b), (b') or (c) are co-cultured with CTSF for a predetermined amount of time in a non-adherent culture vessel.

The present invention is also directed to providing a method for producing de novo papillae comprising the steps of:
(a) providing at least one dermal papilla (DP) from at least one mammal hair follicle,
(b) isolating dermal hair papilla fibroblasts (DPFs) from the DP by mechanically fixing said DP at the surface of a cell culture vessel, whereby the basal lamina is perforated to allow said DPFs migrating out,
(c) expanding the isolated DPFs in monolayer culture without collagen coating, wherein said DPFs are passaged at least once,
(d) condensing the expanded DPFs into cell aggregates that exhibit the size and shape of the physiological DP, wherein said DPFs are differentiated in non-adherent culture vessels in a cell concentration per vessel surface of 1,000 to 100,000 DPFs/cm$^2$, optionally the expanded DPFs are condensed for at least 48 h, and
(e) coating the de novo papillae with extracellular matrix proteins, preferably collagen IV, fibronectin and/or laminin.

The present invention is also directed to providing a method for producing de novo papillae comprising the steps of:
(a) providing at least one dermal papilla (DP) from at least one mammal hair follicle,
(b) isolating dermal hair papilla fibroblasts (DPFs) from the DP by mechanically fixing said DP at the surface of a cell culture vessel, whereby the basal lamina is perforated to allow said DPFs migrating out,
(c) expanding the isolated DPFs in monolayer culture without collagen coating, wherein said DPFs are passaged at least once,
(d) condensing the expanded DPFs into cell aggregates that exhibit the size and shape of the physiological DP, wherein said DPFs are differentiated in non-adherent culture vessels in a cell concentration per vessel surface of 1,000 to 100,000 DPFs/cm$^2$, and wherein the expanded DPFs are condensed for at least 48 h;
(e) optionally coating the de novo papillae with extracellular matrix proteins, preferably collagen IV, fibronectin and/or laminin.

It is particularly the expansion of the isolated DPFs and the physiological administration form that represent limiting factors to the use of these cells in hair growth induction of prior art. It takes several multiplication cycles to achieve the required quantity of cells, during which process the cells cultured in monolayer cultures, especially those of the dermal papilla fibroblasts, lose their inductive abilities, namely, after 5-8 multiplication cycles as shown by experience. The cells thus treated dedifferentiate and express stem cell markers, but can no longer be used to generate hair follicles.

It has been surprisingly demonstrated by the inventors that the cells reach the level of differentiation and stabilization or regain their hair growth-inducing ability after several days to several weeks under the specific culture conditions of the invention, wherein the DPFs expanded following cell culturing are transferred at well-defined concentration into special non-adhesive cell culture vessels. In addition to the regain of inductive properties, it has been surprisingly found that as a result of active cell-cell contacts and exchange of signaling molecules, the cells subsequently form cell aggregates and differentiate. Under these specific conditions, the cells thus treated condense into approximately the shape and size corresponding to the physiological shape of a dermal papilla in a hair follicle following isolation. To this effect, the ratio of cells used/culture vessel surface is of crucial importance.

Prior step (a), a hair follicle is taken from a mammal being a patient or donor. The sample is especially gathered from a human, rodent, pig, canine, monkey, sheep, cat; or dog, preferably a human. It is essentially preferred to gather a tissue sample by skin biopsy, especially taken close to the location of ailment. In the present invention, the sample of the hair follicle is preferably withdrawn from head hair, beard, eyebrows, genital hair or other body hair. The withdrawal of the hair follicle follows good medical practice. The sample may be purified to remove disturbing substances.

The provision of DPs from the hair follicles and the isolation of DPFs according to step (a) proceeds in a form newly developed from previous standard protocols. Using the small pieces of skin biopsies, the epidermis is severed from the underlying dermis and fatty tissue, e.g. by using a scalpel. The fatty tissue is slightly compressed, e.g. by using pincers, so that the hair bulbs located therein are easily prepared under a dissection microscope. Such isolated hair follicles are fixed on the hair shaft, e.g. by means of pincers again, and the connective tissue sheath is carefully separated in a diametrical fashion, e.g. by means of another pair of pincers, so that the bulb is everted to expose the DPFs and the hair shaft with the hair matrix. In this way, the proximal part of the bulb, together with the connective tissue sheath fibroblasts, and the dermal papillae are easily separated from the remaining part of the hair follicle, such as by using a needle or cannula. Also, the hair shaft, which includes the likewise required hair matrix keratinocytes and melanocytes, is optimally prepared for further culturing.

Thereafter in step (b), the isolated dermal papillae are transferred into a cell culture vessel, and mechanically fixed at the surface of the vessel. Preferably, the DPFs are obtained by mechanically arresting the isolated dermal papillae on the culture vessel bottom using a pinpoint or scalpel rather than subjecting them to enzymatic separation. It is preferred to incubate 1 to 8 DPs per culture vessel. Particularly, 2 to 4 DPs are transferred into each well of 6-well or 12-well cell culture plates, for instance, and fixed on the plate bottom. As a result, the basal lamina is slightly perforated, but the papilla morphology is approximately maintained, and the DPFs can migrate out of the dermal papillae, and proliferate.

Culturing of the DPFs in step (c) is effected without collagen coating in standard medium, preferably including a reduced amount of fetal calf serum (FCS), e.g. 10% in contrast to conventional 20% FCS, and additionally supplemented with antibiotics, such as 1× penicillin/streptomycin. Following isolation, the first medium change is preferably effected after 1 week at the earliest, but after 2 weeks at the latest. As soon as cells have grown out of the DP, the medium can be changed once to twice a week, depending on the cell density. When the cells reach 70-80% confluence, they are detached from the plate bottom, for instance by using trypsin/EDTA at room temperature, and passaged into other culture vessels, such as T25 cell culture flasks. In the course of culturing, the cells can be further expanded for direct use in experiments, or frozen in liquid nitrogen for future use. Although the number of passages is not limited, so that cells can be expanded to any high density if viability is given, it is preferred that said DPFs are passaged at least two times, more preferably at least five times, most preferably less than nine times. For a high throughput procedure eight passages are preferred. Consequently, in another preferred embodiment of the present invention, the method is performed by condensing non-inductive DPFs. It is an unexpected finding that such DPFs lacking inductive properties can still be used for tissue engineering.

Next to follow is the condensation phase of step (d), wherein the separated, multiplied DPFs are cultured in non-adherent culture vessels with medium including well-defined components, i.e. standard culture medium. In this system, a special vessel's surface, or a special coating of the vessel surface, especially the bottom surface, reduces the cell attachment or even prevents the cells from attaching to the surface. Preferably, the non-adhesive culture vessels are made of glass, polystyrol, and/or a surface treated with an anti-adhesion layer. More preferably, a PTFE- or poly-HEMA-coated surface is applied in the vessels. The use of ultra-low attachment culture vessels is particularly preferred in the scope of the invention, which are e.g. distributed by Corning, Inc., USA. Such non-adherent vessels and coatings are known to the skilled artisan, and can be easily purchased, or manufactured.

As a result of free contacting, the cells aggregate into a defined size, forming aggregates after several days which resemble the original papilla in size and shape. The expanded DPFs are preferably condensed for at least 48 hours, 2 to 5 days, more preferably for 2 to 3 days, most preferably substantially 2 days, and optionally further cultivated for 3 to 15 days, preferably for 5 to 10 days or 2 to 21 days. Size and shape of the condensates being formed likewise depend on the region where skin biopsies have been removed. DPFs, which are removed from beard, body hair, eyebrows, genital hair, or head hair, and subjected to expansion form cell aggregates of different size, which in turn determine the respective hair shape, size and length. Even more crucial is the initial cell number as inoculated into the vessel, which has to be in due proportion to the vessel surface. In another embodiment of the method, the cell concentration per vessel surface amounts to 2,000 to 50,000 DPFs/cm$^2$ in step (d), preferably 3,000 to 20,000 DPFs/cm$^2$, more preferably 5,000 to 10,000 DPFs/cm$^2$, most preferably substantially 6666 DPFs/cm$^2$.

At this stage, a self-produced matrix has already formed around the condensate. To accelerate this process and exert influence thereon in a targeted manner, physiologic matrix components are added to the medium at this point to form a capsule mimicking the properties of a dermal papilla. In the subsequent process step (e), the de novo papillae thus obtained are coated with a composition of extracellular matrix proteins. This composition is made so as to mimic physiological ones. It may preferably consist of collagen IV, fibronectin and/or laminin. It is particularly preferred that the extracellular matrix proteins are a mixture of collagen IV, fibronectin and laminin in shares of 2-6:0.5-2:0.5-2 parts per weight, most preferably having a ratio of substantially 4:1:1.15 parts per weight. It is not excluded, however, that the aforementioned extracellular matrix proteins can also be used individually or with varying volume percentages or combined with other matrices. In another embodiment of the invention, the extracellular matrix proteins additionally comprise other collagens (eg. 1, 10 A1, 18 A1), glycosaminoglycans and/or proteoglycans, preferably heparan sulfate, decorin, keratan sulfate, biglycan, aggrecan, versican, perlecan, CD44v3, and/or syndecan. Again, such coating of the neopapillae is carried out in a minimally adhesive cell culture vessel, e.g. ultra-low attachment cell culture vessels. The coating is performed for 1 to 5 days, preferably for 1 to 2 days.

The present invention also relates to the de novo papillae, and the hair microfollicles obtainable by the processes according to the invention. The prior teaching of the present specification concerning the methods for producing neopapillae and microfollicles, respectively, is considered as valid and applicable without restrictions to the products of the production methods if expedient.

Both, the de novo papillae and/or hair microfollicles of the invention can be used for the production of skin equivalents. Preferably, the skin equivalents are constructed, such as by using Matriderm (Dr. Suwelack Skin & Health Care AG), according to standard methods, and the insertion sites for the microfollicles are cut at regular intervals by means of a 2-photon laser, or pre-perforated with a punch. Consequently, skin equivalents comprising the de novo papillae and/or hair microfollicles of the invention are another object of the invention. In addition to the reconstructed dermal papillae, they comprise one or more layers of keratinocytes, which may form themselves into an epidermal structure, or peridermal structure, and optionally one or more layers of melanocytes, which can be applied over the dermal papilla structure.

The de novo papillae and/or the hair microfollicles according to the invention can also be used as implants. Therefore, still another object of the invention is an implant comprising as active ingredient an effective amount of the de novo papillae of the invention and/or the hair microfollicles of the invention, optionally together with pharmaceutically tolerable adjuvants.

Similarly, the skin equivalent of the invention can be used as transplant. It is still another object of the invention to provide a transplant comprising as active ingredient an effective amount of the skin equivalent according to the invention, optionally together with pharmaceutically tolerable adjuvants.

The term "effective amount" denotes an amount of the implant or transplant, respectively, having a prophylactically or therapeutically relevant effect on a disease or pathological conditions. A prophylactic effect prevents the outbreak of a disease or even the infection with a pathogen after the infiltration of single representatives such that the subsequent propagation of the pathogen is strictly diminished, or it is even completely inactivated. A therapeutically relevant effect relieves to some extent one or more symptoms of a disease or returns to normal either partially or completely one or more physiological or biochemical parameters associated with or causative of the disease or pathological conditions. The respective amount for administering the implant or transplant, respectively, is sufficiently high in order to achieve the desired prophylactic or therapeutic effect of reducing symptoms of reduced amount of hair. It will be understood that the specific dose level, frequency and period of administration to any particular mammal will depend upon a variety of factors including the activity of the specific components employed, the age, body weight, general health, sex, diet time of administration, route of administration, drug combination, and the severity of the specific therapy. Using well-known means and methods, the exact amount can be determined by one of skill in the art as a matter of routine experimentation.

The implants or transplants of the invention are produced in a known way using common solid or liquid carriers, diluents and/or additives and usual adjuvants for pharmaceutical engineering and with an appropriate amount depending on the intended mode of application. These pharmaceutically acceptable excipients comprise salts, buffers, fillers, chelating agents, antioxidants, solvents, bonding agents, lubricants, coatings, additives, preservatives, and suspending agents. In the meaning of the invention, an "adjuvant" denotes every substance that enables, intensifies or modifies a specific body response as result of implanting or transplanting if administered simultaneously, contemporarily or sequentially. The amount of excipient material that is combined with the active ingredient to produce a single dosage form varies depending upon the host treated and the particular mode of administration.

Depending upon the manner of introduction, the implant or transplant, respectively, may be formulated in a variety of ways. The concentration of therapeutically active ingredients in the formulation may vary from about 0.1 to 100 wt %. They may be administered alone or in combination with other treatments.

The invention also teaches de novo papillae, hair microfollicles and/or skin equivalents according to the invention for the prophylactic or therapeutic treatment of a condition of reduced amount of hair. The aforementioned products of the inventive methods are preferably used for the therapeutic treatment. A therapeutically relevant effect relieves to some extent one or more symptoms of a reduced amount of hair, or returns to normality, either partially or completely, one or more physiological parameters associated with or causative of the pathological conditions. Monitoring is considered as a kind of treatment provided that the products of the inventive methods are administered in distinct intervals, e.g. in order to booster the proliferation response and eradicate the symptoms of the condition completely. Either identical products or different products can be applied. In the meaning of the invention, prophylactic treatment is advisable if the subject possesses any preconditions for the beginning of hair loss, such as a familial disposition, a genetic defect, or a previously passed disease.

The pathologic conditions of a reduced amount of hair as concerned by the invention may be the result of alopecia (e.g. androgenetic alopecia, alopecia greata, etc.), hereditary baldness, scarring, burns, radiation therapy, chemotherapy, disease-related loss of hair, accidental injury, damage to hair follicle, surgical trauma, an incisional wound, or a donor site wound from a skin transplant.

The invention also relates to the use of the de novo papillae, hair microfollicles and/or skin equivalents according to the invention for the production of an implant or transplant, respectively, for the prophylactic or therapeutic treatment of a condition of reduced amount of hair. The implant and transplant can be either administered to prevent the initiation of hair loss of a mammal, preferably a human individual, and the resulting trouble in advance, or to treat the arising and continuing symptoms.

It is another object of the invention to provide a method for treating a condition of reduced amount of hair, wherein the de novo papillae, hair microfollicles and/or skin equivalents according to the invention are incorporated into the skin of a mammal in need of such treatment. The microorganoid follicles, especially autologous/allogenic human hair follicle precursors, are used for implantation with the aim of inducing hair growth, whereas the skin substitutes do regenerate skin, preferably the scalp. The microorganoid follicles are incorporated into the openings of previously depilated, miniaturized hair follicles (isthmus) of affected skin areas. Preferably, the de novo papillae and hair microfollicles are injected, more preferably by means of a specially constructed device of about 150 µm in size. It is also preferred that all components are used in an autologous fashion, and treated under GLP/GMP conditions. The neopapillae, hair microfollicles, or hair follicle compartments stimulate the new development of hair growth, such as in cases of hereditary baldness, scarring (burns), disease-related loss of hair, chemotherapy/radiation-induced loss of hair, and the like as already described in the course of the present specification. Maturing of the microfollicles into hair follicles having long-term viability is fostered by the micro-medium, i.e. the permanent, distal hair follicle.

The invention also relates to the use of the aforementioned products for the direct pharmacological and cosmetic in vitro testing of substances, which exert a hair-modulating influence. The hair-modulating effects are especially selected from the group of hair growth, hair shape, hair structure, hair color, and hair pigmentation. It is preferred to analyze the effect of modifying hair growth—with the intention of promoting hair growth in cases of hair loss, such as caused by alopecia, as well as inhibiting hair growth in cases of excessive, undesirable hair growth, such as caused by hypertrichosis and/or hirsutism, or female beard growth, or undesirable body hair. In particular, the use of a high-throughput method allows the pharmaceutical and cosmetic industries to effectively test existing or new substances for a potential hair growth-modulating effect. The substances comprise pharmaceutical agents, cosmetic agents, chemical compounds, polymeric compounds, growth factors, cellular products, living cells and/or biomolecules. Furthermore, when adding melanocytes, i.e. the pigment-forming cells, to the microfollicles, it is possible to investigate substance effects on the pigmentation and/or coloring of the hair shaft being formed. Likewise, the substance effect on hair shape and hair structure can be tested, e.g. formation of curls, etc.

The following end points can be evaluated or measured to obtain information on the effectiveness of substances in regard to an improvement in hair structure and the influencing of hair growth: analysis of hair shaft formation, length growth and characteristics of the hair shaft, hair array analysis, volume and structure of the dermal papilla, proliferation measurement (e.g. Ki67 expression, BrdU incorporation, etc.), apoptosis measurement (e.g. TUNEL, enzyme assays, annexin measurement, etc.), differential marker analysis (e.g. immunhistology, in situ hybridization, RT-PCR, etc.), determination of alkaline phosphatase as DPF marker, analysis of certain hair-specific proteins (e.g. hair-specific keratins, etc.), analysis of cytokines, growth factors, chemokines and all kinds of messenger substances formed inter alia by the dermal papilla (e.g. by BioPlex, ELISA, etc.), and/or proteome or expression analysis of matrix proteins, growth factors (e.g. MSP, HGF, CTGF, etc.), transcription factors, molecules of the wnt-pathway (e.g. DKK1, BMP2-4, etc.), interleukins (e.g. IL-6, etc.) and/or chemokines/chemokine receptors (e.g. CXCR, etc.), which exhibit an enhanced appearance, as well as apoptosis-inducing molecules and/or proliferation-stimulating molecules, which exhibit a reduced appearance. The influence on hair pigmentation can be measured by means of arrangement/migration of melanocytes, melanin granula formation/distribution, and the activity of tyrosinase and/or array analysis of gene expression involved in melanin synthesis. Other embodiments, modifications and variations of the present invention will be readily apparent to the expert on reading the specification and can be put into practice without departing from the scope of the invention.

Furthermore, the de novo papillae or microfollicles of the invention can be used separately, or in connection with the generation of skin equivalents with hair follicles, for the pharmacological and toxicological in vitro testing of substances in medicine, pharmacy, and beauty culture. Such use, e.g. performed as high-throughput method, is of special interest for the pharmaceutical, chemical and cosmetic industries if obliged to test their substances and products for toxic effects. New legal instructions demand replacement of previous animal tests by suitable in vitro test methods. Therefore, the microfollicles themselves, but also, artificial skin replacement systems with integrated microfollicles can be employed as ideal screening systems for toxicological investigations including irritations, genotoxic effects, etc. The model structures of the invention may completely replace animal tests, as well as substitute less suitable in vitro models being currently available, since the present models make the analysis of complex physiological processes possible. Such tests can be performed by exposing the model structure to a substance of interest in a bioreactor. Following a substance-specific incubation period, which is particularly between 3 minutes and 4 hours, the model is washed with medium, and subsequently analyzed by suitable assays exemplarily described in the prior course of the specification.

The present invention additionally teaches a method for screening substances, which modulate hair properties, comprising the steps of providing a sample of the de novo papillae, hair microfollicles and/or skin equivalent according to the invention, dividing the respective sample into portions, incubating at least one portion with substances to be screened, and comparing parameters of hair properties in the portion with another portion that is not incubated with the substances. Briefly, the inventive method makes the identification and analysis of substances possible, which exert an influence on hair via the model structures of the invention. The sample, which shall be understood to comprise a certain number of product subjects according to the invention, is divided into multiple portions. At least two subsets are provided; one is used for screening while the other one serves as negative control. Preferably, the number of screening parts exceeds the number of control parts. Usually, numerous portions are subjected to a high-throughput screening. The substances to be screened in the inventive method are not restricted anyway. In an embodiment of the invention, the substances are selected from the group of nucleic acids including RNAi, rybozymes, aptamers, antibodies, peptides, carbohydrates, polymers, small molecules having a molecular weight between 50 and 1,000 Da, and proteins, preferably antibodies, cytokines and lipocalins. These substances are often available in libraries. It is preferred to incubate a single compound within a distinct portion of the sample. However, it is also possible to investigate the cooperative effect of substances by incubating at least two substances within one portion. A further subset of subjects is simultaneously incubated in the absence of the substances. The incubation process depends on various parameters, e.g. the cell types and the sensitivity of detection, which optimization follows routine procedures known to those skilled in the art. The identification of effective substances in the meaning of the invention is indirectly performed, preferably by determining the expression patterns and/or the cell viability, which are altered. The determination is performed at a specified moment and correlated to the signal strength at the beginning of the experiment and the negative control. Suitable tests are known to those skilled in the art or can be easily designed as a matter of routine.

Further, the invention may be practiced as a kit comprising the de novo papillae, hair microfollicles, skin equivalent, implant and/or transplant according to the invention, particularly in order to perform the inventive methods of treating a condition of reduced amount of hair, or screening substances, respectively. The kit of the invention may include an article that comprises written instructions, or directs the user to written instructions for how to practice the methods of the invention. For further details, reference may be made to the foregoing observations on the treatment method as well as the screening method according to the invention, which also apply accordingly to the kit of the invention.

In the scope of the present invention, methods for producing de novo papillae and hair microfollicle, which applies the condensing of expanded DPFs into physiological cell aggregates by means of three-dimensional cultivation and a certain ratio of cell concentration to vessel surface, is provided for the first time. As seen from the formation of hair shaft-producing microfollicles, and by means of gene and protein expression analyses, the DPFs reassume their original, inductive properties after specific condensation. Since the inductive properties of cells can be re-established in the course of the present method, the number of passages to expand cells does not matter. Thus, it is advantageously possible to use constant and high numbers of starting cells and carry out controlled supply of media in a reproducible fashion when using three-dimensional culturing in non-adherent culture vessels. Compared to other 3D culturing methods for general differentiation experiments, such as micro-mass, pellet culture or the hanging drop method, the cells in the culturing system of the invention are not forced into cell-cell contact, but are allowed to associate individually to form cell aggregates and, in the event of DPFs, papilla-like condensates.

The provision of the de novo papillae, hair microfollicles and skin equivalents as defined by the production process results in implants or transplants, respectively, for the prophylactic or therapeutic treatment of conditions of reduced amount of hair. The present products of the invention afford a number of advantages. Both, the hair follicle equivalent and the skin substitute are more standardizable than the isolated hair follicle. They reduce the demand for hair follicles and are closer to the in vivo situation than any prior art model. The complex three-dimensional models of the invention simulate the hair follicle in vivo in its structure and histological composition, resulting in a high level of relevance of the information provided on the effectiveness and compatibility of active substances. All products of the invention are further characterized by a high stability, low manufacturing costs, convenient handling, and are available at any time. These features form the basis for a reproducible action in standardized protocols, and for a reliable and safe interaction with their matching effector molecules. Their use is a promising, novel approach for a broad spectrum of therapies causing a direct and immediate reduction of symptoms.

The products according to the invention are suitable for various applications in the medical, pharmaceutical and cosmetic fields, such as for the development of cosmetic products, or for the discovery of active substances with a biological effect on the hair follicle by influencing hair pigmentation, hair growth, hair structure, and the like, which may be performed in in vitro test systems or screening processes, thereby providing information on the effect of substances on hair follicle cells with in vivo relevance. The provision of the products thus formed is of particular benefit for large-scale screening tests. All of them can be employed in screening procedures suitable for high throughput to identify active substances, or active substance compositions for growth promotion or growth inhibition of hair, and in toxicological testing of substances and chemicals. The production methods as well as arising screening methods of the invention can be performed in a simple and fast manner. In addition, the appropriate kit is cost-efficiently produced.

It is to be understood that this invention is not limited to the particular methods, products, kit or uses described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a vessel" includes a single or more vessels, which can be either identically or differently sized, shaped or composed, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used.

BRIEF DESCRIPTION OF THE DRAWINGS

Figures

FIG. 1 shows:
A) Punch biopsy of a donor skin taken from a lifting surgery. The dashed line indicates the cutting line of the dermosubcutaneous border for further hair follicle isolation.
B) The "amputated" and dissected hair follicle (highlighted box) is dissociated by a novel technique: The connected tissue sheath is pulled diametrically over the hair shaft resulting in a pure separation of the hair shaft with outer and inner root sheath keratinocytes and melanocytes on the on hand and Dermal papilla and connective tissue sheath on the other hand.
C) Dissected connective tissue sheath with its fibroblasts plus adjacent dermal papilla, which can accurately, been cut off (highlighted box).
D) A dissected dermal papilla taken by electron microscopy.
E) Outgrowth of dermal papilla fibroblast from the slightly scratched and anchored dermal papilla, leaving their capsule structure almost intact.
F) Cultured dermal papilla fibroblast of the $3^{rd}$ passage in uncoated culture 75 $cm^2$ flasks.
G) Dermal papilla fibroblast forming dermal papilla-like condensates on ultra low attachment 75 $cm^2$ flasks.
H) Magnification of a dermal papilla fibroblast condensation ready to be processed to a Neopapilla with extracellular matrix components in 6well low attachment plates.

FIG. 2 shows:
A) Neopapilla (white arrow) with extracellular matrix and surrounded keratinocytes, which have been added to the ultra low attachment plate forming a multi-cellular condensate.
B) First signs of the formation of follicular structures after 24 h in ultra low attachment culture.
C) Neofollicle formation after 1 week. Clearly visible is the formation of a primitive hair shaft.
D) Neofolllicle formation taken by DIC light microscopy illustrating the intact dermal papilla structure after 1 week of culture.
E) Neofollicles inserted in a skin equivalent showing defined hair follicle like structures. The highlighted box shows a down-growing hair follicle. With the inverted microscope you see the proximal portion of the follicle/skin equivalent.
F) Further culture of the Neofollicles within the skin equivalent demonstrating a clear anchorage of the hair follicle and continued growth.

FIG. 3 shows:
Neofollicle produced using KC and MC derived from sources different than mammalian hair follicle durich different stages of development and formation:
A) Stage 1: Neopapilla (without the addition of exogenous extracellular matrix proteins) surrounded by Melanocytes and keratinocytes, which have been added to the ultra low attachment plate forming a early multi-cellular condensate.
B) Stage 2: First signs of the formation of follicular structures after 24 h in ultra low attachment culture (Note the protuberance on top). The attached Cells adhere to the Neopapilla and adopt a flattened shape
C) Stage 3: Beginning Neofollicle formation after 1 week with hair follicle-like sheath development.
D) Stage 4: Within the Neofolllicle a clearly visible formation of a primitive hair shaft becomes visible.

DETAILED DESCRIPTION OF THE PRESENTLY PREFERRED EMBODIMENTS

Examples

Example 1

Isolation and Culture of Human Follicular Dermal Papilla Fibroblasts (DPF), Connective Tissue Sheath Fibroblasts (CTSF), Keratinocytes (KC), and Melanocytes (MC)

Single hair follicles were obtained after micro-dissection of human scalp samples from excess of lifting surgeries, received under required regulations. To isolate matrix KC and MC, CTSF and fibroblasts of the dermal papilla (DPF), the skin was cut at the dermosubcutaneous interface with a scalpel and hair follicles at anagen stage (growing phase) were pull out with forceps under a dissecting microscope.

In contrast to previously described isolation techniques (e.g. Magerl et al., Methods Exp. Dermat. 11, 381-385, 2002), pure fractions of the desired cell populations, were obtained by longitudinally slicing the connective tissue of the upper part of the dissected hair follicle. By fixing the hair shaft on the one site, the CTS can be diametrically pulled over the hair matrix with forceps towards the lower proximal portion. With this technique DP cells were automatically uncovered avoiding damage and mixing cell types. Thus, the CTS and the dermal papilla as well as the hair matrix containing KC and MC cells were clearly separated and can easily been cut off by a scalpel.

DP and CTS isolates were separately cultured into 6-well cell culture plates (2-4 in one well) by fixing them to the culture plate with a needle. To enable a fast outgrowth but keeping the capsule morphology and niche of the fibroblast at the same time, the thin membrane was slightly scratched to loosen extracellular matrix components (ECM). The cells were submerged with DMEM+ (Gibco/Invitrogen) plus 10% fetal calf serum (FCS) until growth of fibroblast was observed after 1-2 weeks based on donor variations. The cells were then moved to a 25 cm2 culture flask for another week and were further passaged to a 75 cm$^2$ culture flask. After reaching sub-confluence passage 3 were split into three 75 cm$^2$-flasks obtaining 1.5-2 million DPF or CTSF, respectively.

The KC and amelanotic hair follicle MC were removed from the remaining hair shaft and the attached hair matrix by trypsinisation (0.05% trypsin and 0.53 mM EDTA) and were separated by differential trypsinisation and cultured with standard methods as described in Tobin et al., J. Invest. Dermatology 104(1), 86-88, 1995.

Example 2

Formation of Neopapillae

The optimized count of 500,000 DPF were seeded into a 75 cm$^2$ ultra-low attachment culture flask (Corning) containing DMEM+ and were allowed to form cell aggregates. After 48 hours keeping them unmoved these aggregates shape the size of a native human hair follicle dermal papilla. Condensates were then transferred to a 6-well ultra-low attachment plate and a mixture of Laminin (final concentration 11.5 µg/ml), Fibronectin (final concentration 10 µg/ml) and Collagen IV (final concentration 40 µg/ml) is added to the wells. After 24-48 hours in culture, intrinsic ECM secretion and the added proteins built a stable matrix envelop and Neopapillae have formed. To facilitate faster ECM accumulation and differentiation, growth factors i.e. Hepatocyte Growth Factor (30 ng/ml) and/or Connective Tissue Growth Factor (20 ng/ml) can alternatively been added to the medium. These Neopapillae are ready to be implanted into skin in vivo to develop hair inductive properties.

Example 3

Formation of Neofollicles 250,000 KC and MC (10:1) were added to the Neopapillae in ultra-low attachment culture flask (6 well, Corning) and DMEM+ Medium was changed to Defined Keratinocyte Serum-Free Medium (Gibco). After 1 week the covered Neopapillae form hair follicle like structures. These Neofollicles could already been used for testing. To elaborate a multilayered Neofollicle, which even better mimics hair follicle structure and function can be obtained by coating the generated Neofollicle with a mixture of collagen IV (60 µg/ml) with CTSF (200,000 cells) in ultra low attachment plates with DMEM+ 10% FCS for further 2 days and change of medium every further 3rd day.

Example 4

Generation of Skin Equivalents with Neofollicles

Juvenile Human Foreskin Fibroblasts were isolated using previously described methods (Toma et al., Stem Cells 23, 727-37, 2005) and cultured in DMEM+ 10% FCS. 250,000 dermal fibroblast (also DPF or CTSF were used, but foreskin fibroblasts were preferred for handling reasons) were mixed to a Fibrinogen solution (Sigma, 3 mg/ml) and 2.0% (v/v) Aprotinin (20 µg/ml) and 2.5% (v/v) Thrombin 1.25 U/ml were added. This chilled solution was filled in transwell culture chambers avoiding air bubbles. After adjusting the temperature for 2-3 min at room temperature, 30-40 Neofollicles were gently introduced to the solution and polymerization to a gel was done for 10 min at 37° C. The composed matrix was soaked with DMEM+ medium for 48 h.

Dermal Keratinocytes were isolated from skin biopsies obtained from face lift surgeries or from foreskin (Barrandon & Green, Proc Natl. Acad. Sci. 82, 5390-4, 1985). Briefly, the underlying fatty tissue and dermis were cut off and the remaining epidermis was digested overnight in a Trypsin/EDTA solution (PAA) at 4° C. KC were harvested using a cell scraper and after passing through a 70 µm cell strainer (Becton Dickinson) they were seeded onto collagen I coated culture flasks. Defined Keratinocyte Serum-Free Medium (Gibco) was changed twice a week and KC were passaged or harvested at 60-80% confluence.

KC (250,000) were added on top of the matrix and let them adhere for 24 hours. Excessive cells were taken by changing the Defined Keratinocyte Serum-Free Medium (Gibco) and after having reached confluence, the transwell chambers were lifted to the air-liquid interphase to enable KC differentiation.

Also cell lines (i.e. HaCat for KC and HS27 for fibroblasts) were tested for generating a similar skin model as they are easier to culture and reduce donor variations. They were grown in DMEM+ (Gibco) supplemented with 5% fetal calf serum (FCS, Gibco).

Example 5

Formation of Neofollicles Comprising Cells not Derived from Mammalian Hair Follicles Neofollicles have been prepared as described in Example 3 using KC and MC obtained as outlined below.

Cell Culture Human Foreskin Keratinocytes and Fibroblasts:

Human Foreskin Fibroblasts and Keratinocytes were isolated from circumcisions using previously described methods (Toma et al., Stem Cells 23, 727-37, 2005, Barrandon and Green, Proc Natl Acad Sci. 1985, 82:5390-4.). Briefly the underlying fatty tissue and dermis were cut off and the remaining epidermis was digested overnight in a Dispase solution (4 mg/ml, Sigma) at 4° C. overnight. Keratinocytes were then harvested using a cell scraper and after passing through a 70 µm cell strainer (Becton Dickinson) are then seeded into culture flasks. All Keratinocytes were grown in Collagen I coated cell culture flasks and Defined Keratinocyte Serum-Free Medium (Gibco). Medium was changed twice a week and the Keratinocytes were passaged or harvested at 60-80% confluence. Fibroblasts were cultured in DMEM+ 10% FCS.

Cell Culture Human Epidermal Melanocytes:

Starting from a cryovial of Human Adult Epidermal Melanocytes (purchased from CellMade) cell culture procedures were done according to the manufacturers protocol. Briefly, 15 ml Melanocytes Growth Medium was added to a T75 culture flask. The cells were thawed quickly by placing the lower half of the vial in a 37° C. water bath for 1 minute. The cells were the resuspended in into the T-75 flask containing Melanocytes Growth medium. The T-75 flask was placed in a 37° C., 5% CO2 humidified incubator. The Melanocytes Growth Medium was changed every 2-3 days. The cells were subcultured when the culture reached 80% confluent.

Figure 1:
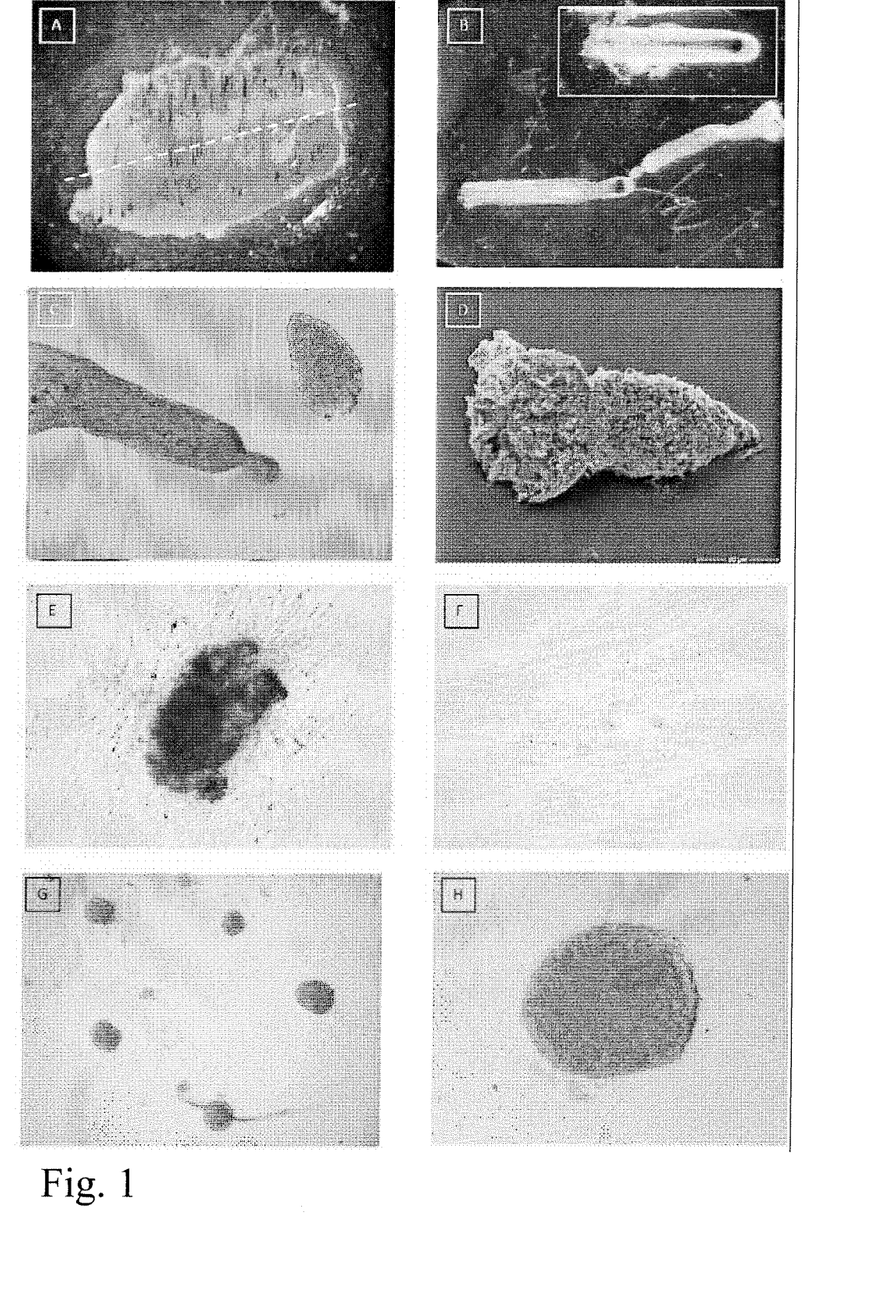
Figure 2:
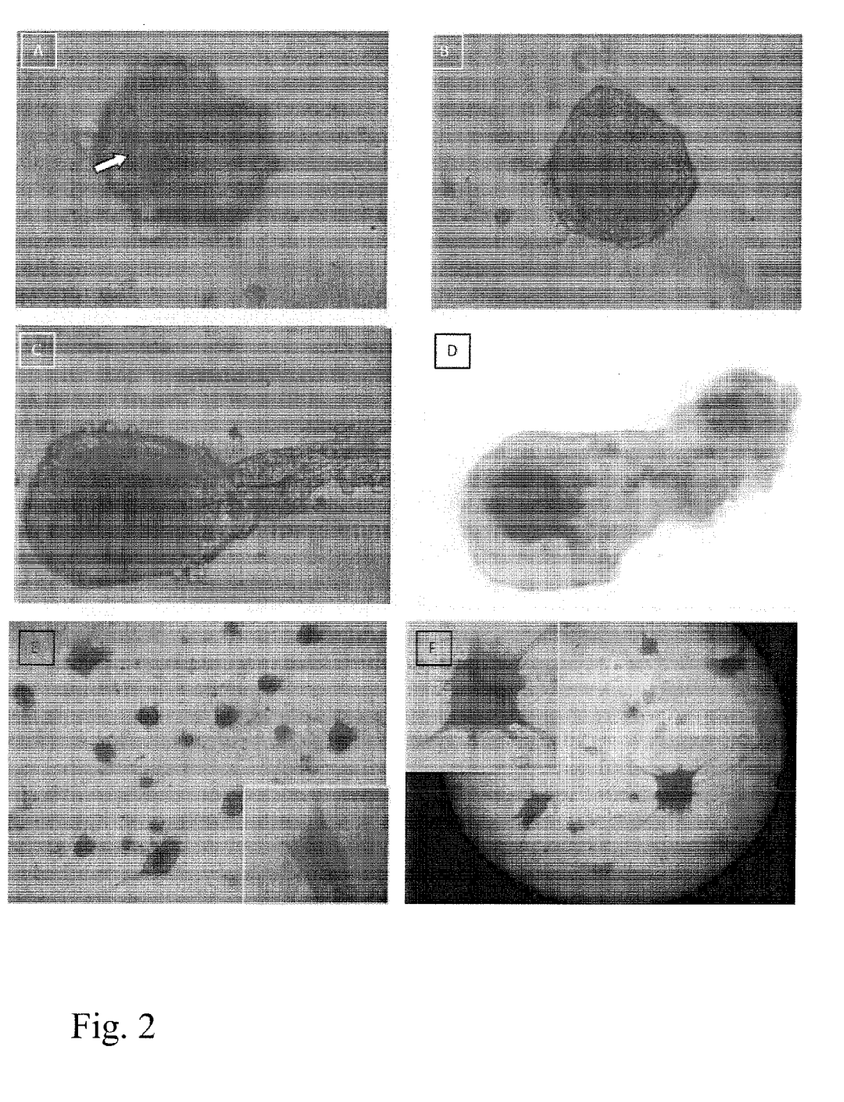
Figure 3:
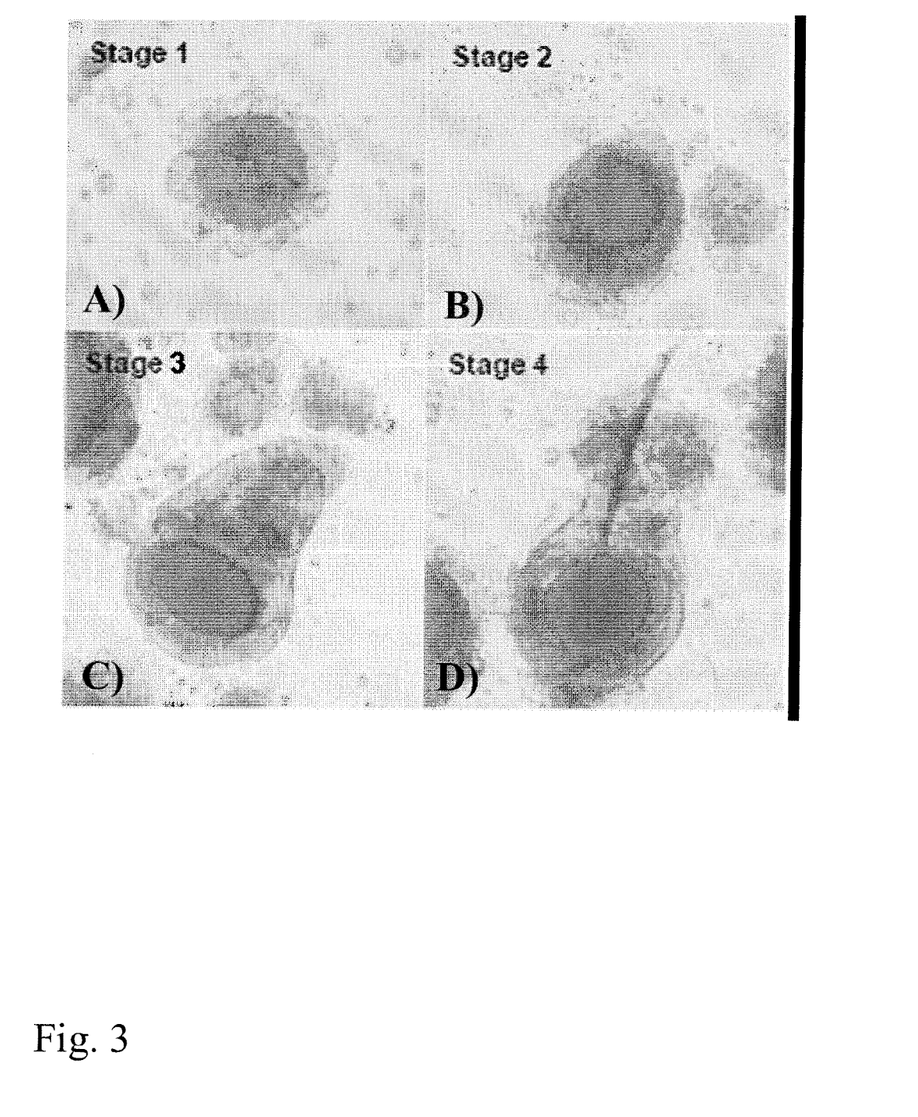
Figure 4:
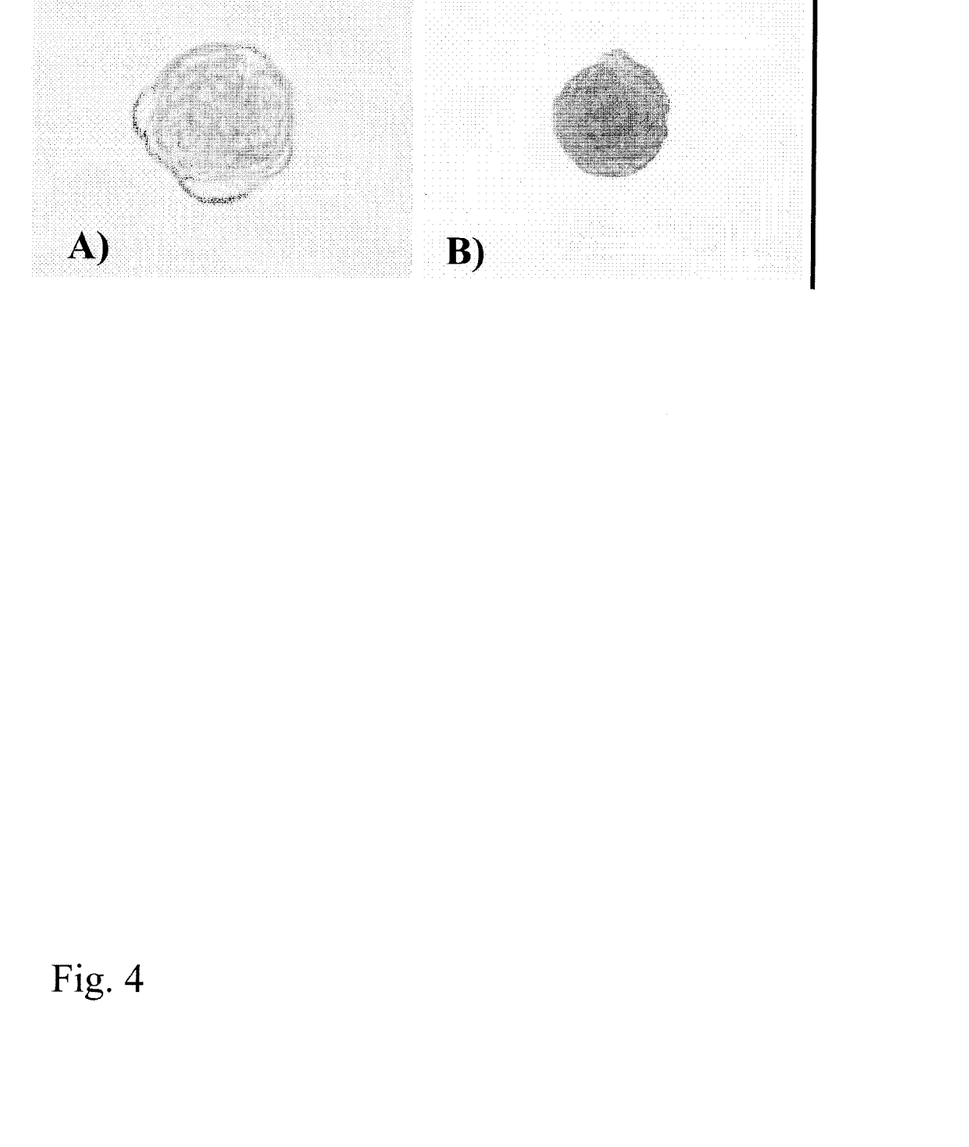
FIG. 4 shows:
Formation of functional neopapillae at two different time points;
A) after 48 hours condensation; and
B) after 7 days of condensation; at day 7, the aggregation of cells is much more dense and the formation of self derived extracellular matrix becomes visible.

Resulting neofollicles are depicted in FIG. 3. were the different stages of development of Neofollicles produced using KC and MC derived from sources different than mammalian hair follicle are shown. In stage 1, Neopapilla (without the addition of exogenous extracellular matrix proteins) are surrounded by Melanocytes and keratinocytes, which have been added to the ultra low attachment plate forming a early multi-cellular condensate. A loose aggregate has been created. In stage 2, first signs of the formation of follicular structures in ultra low attachment culture can be seen. The attached cells adhere to the Neopapilla and adopt a flattened shape while a protuberance has been built on top of the condensate. After approximately 1 week, the Neofollicle begins to form comprising hair follicle-like sheaths development. Within the established Neofolllicle, a clearly visible primitive hair shaft becomes visible.

Example 5

Gene Expression Analysis of Different Human Dermal Papilla Derived Cell Samples Using Agilent Whole Human Genome Oligo Microarrays (One-Color)

1. SuperAmp™ RNA Amplification

Two isolated native Dermal Papillae, $1 \times 10^3$ monolayer-cultured Dermal Papilla Fibroblasts, re-condensed Dermal Papilla Fibroblasts after 48 hours and re-condensed Dermal Papilla Fibroblasts after 14 days were prepared as described above. The Four human cell samples were lysed using SuperAmp™ Lysis Buffer.

TABLE 2

List of samples

| Sample no. | Cell sample | ID |
|---|---|---|
| 1 | DP | 1 |
| 2 | MONO | 2 |
| 3 | KOND 1 | 3 |
| 4 | KOND 2 | 4 |

SuperAmp RNA amplification was performed according to Miltenyi Biotec's procedure. Briefly, the amplification is based on a global PCR protocol using mRNA-derived cDNA. mRNA was isolated via magnetic bead technology. Amplified cDNA samples were quantified using the ND-1000 Spectrophotometer (NanoDrop Technologies).

TABLE 3

Summary of cDNA yields

| Cell sample | Concentration (ng/μL) | Ratio (260/280) | Volume (μl) | Total amount of cDNA (μg) |
|---|---|---|---|---|
| 1 | 161.92 | 1.81 | 20 | 3.2 |
| 2 | 143.79 | 1.86 | 20 | 2.9 |
| 3 | 123.05 | 1.83 | 20 | 2.5 |
| 4 | 117.41 | 1.84 | 20 | 2.3 |

The integrity of the cDNA was checked via the Agilent 2100 Bioanalyzer platform (Agilent Technologies). The results of the Bioanalyzer run have been analysed using a gel image and an electropherogram using the Agilent 2100 Bioanalyzer expert software. The average length of the highly amplified cDNA products ranged between 200-1,000 bp.

2. Hybridization of Agilent Whole Genome Oligo Microarrays 250 ng of each of the cDNAs were used as template for Cy3 labeling which was performed according to Miltenyi Biotec's protocol. The Cy3-labeled cDNAs were hybridized overnight (17 hours, 65° C.) to an Agilent Whole Human Genome Oligo Microarrays 4×44K (table 4) using Agilent's recommended hybridization chamber and oven.

TABLE 4

Hybridisation schedule

| Experiment no. | Cy3 | Microarray no. |
|---|---|---|
| 1 | 1 | 251485031842_1_1 |
| 2 | 2 | 251485031842_1_2 |
| 3 | 3 | 251485031842_1_3 |
| 4 | 4 | 251485031842_1_4 |

Finally, the microarrays were washed once with 6×SSPE buffer containing 0.005% N-lauroylsarcosine for 1 min at room temperature followed by a second wash with pre-heated 0.06×SSPE buffer (37° C.) containing 0.005% N-lauroylsarcosine for 1 min. The last washing step was performed with acetonitrile for 30 sec.

3. Scanning Results

Fluorescence signals of the hybridized Agilent Microarrays were detected using Agilent's Microarray Scanner System (Agilent Technologies).

4. Image and Data Analysis

The Agilent Feature Extraction Software (FES) was used to read out and process the microarray image files. The software determines feature intensities (including background subtraction), rejects outliers and calculates statistical confidences. For determination of differential gene expression FES derived output data files were further analyzed using the Rosetta Resolver® gene expression data analysis system (Rosetta Biosoftware). This software offers—among other features—the possibility to compare two single intensity profiles in a ratio experiment. All samples were labeled with Cy3, here, the ratio experiments are designated as control versus (vs.) sample experiments (automated data output of the Resolver® system). Please note, that the ratios are always calculated by dividing sample signal intensity through control signal intensity.

5. Gene Lists Single-Experiment Raw Data List Single-Experiment Normalized Data List Gene Ratio List/Pre-Selected Candidate Gene List The output data of the Agilent Feature Extraction software includes gene lists with the complete raw data sets, referred to as single-experiment raw data list. Furthermore, the signal intensities from the single-experiment raw data lists are normalized by dividing the intensity values by their median. These normalized signal intensities are joined to a common table the single-experiment normalized data list. This list comprises in addition to the normalized intensity values the feature glsPosAndSignif which indicates with a value=1 that the signal intensity is positive and significant above the background and a value=0 that the signal intensity is not positive and significant above the background. The Resolver® Software allows the export of a gene list with all normalized sample/controllog10 ratios and -fold changes, sequence descriptions, p-values, etc., referred to as gene ratio list (of all genes). For example: A "−10 fold change" in the gene ratio lists therefore indicates a 10-fold higher gene expression in the control compared to the sample. Putative candidate genes with a fold change >2 and p-value <0.01 are summarized in a pre-selected candidate gene list. An extract of such a list comprising some of the differentially expressed genes is shown in table 5.

TABLE 5

Level (Ratio) of defined genes measured by microarray analysis within fibroblasts (monolayered, condensed 48 hours, condensed 14 days) compared to native dermal papilla fibroblasts.

| Gene Name | Cellular Function | Ratio Mono | Ratio 48 h | Ratio 14 d | Biological Process |
|---|---|---|---|---|---|
| COMP | Matrix | −26.07 | −100 | −16 | noncollagenous extracellular matrix glycoprotein, matrix integrity, cell adhesion |
| MMP10 | Matrix | −43.08 | −12.25 | 8.47 | matrix metalloproteinase (MMP) family are involved in the of extracellular matrix (tissue) remodeling |
| MGP | Matrix | −100 | −8.25 | −3.87 | Extracellular matrix structural constituent, Multicellular organismal development, Cell differentiation |
| CDK8 | Cell Cycle | 23.89 | 16.07 | 4.47 | member of the cyclin-dependent protein kinase (CDK) family, Regulation of transcription, |
| CDH3 | Adhesion | −100 | −52.61 | −34.49 | Zinc ion binding, Regulation of transcription, |
| PCDH85 | Adhesion | −100 | −100 | −10.12 | Protocadherin beta 5, specify differential cell-cell connections |
| L1CAM | Adhesion | 22.49 | 7.95 | −1.65 | Regulation of actin cytoskeleton |
| PCDH20 | Adhesion | −28.97 | −27.7 | 1.76 | Protocadherin 2D, establishment and function of specific cell-cell connections |
| PECAM1 | Adhesion | −71.51 | −100 | −46.87 | Cell to Cell Adhesion Signaling |
| Jag2 | Cytokine | −100 | −100 | −21 | Impact in: cell differentiation, Notch signaling pathway, Regulation of apoptosis, cell proliferation, Cell communication, Multicellular organismal development, Cell cycle, Cell fate determination, Morphogenesis of embryonic epithelium, cell adhesion, cell migration |
| TNFSF10 | Cytokine | −75 | −100 | −10.24 | Apoptosis |
| LEF1 | Transcription Factor | −100 | −100 | −8.5 | LEF1 is a nuclear protein, Regulation of Wnt receptor signaling pathway |
| SPRY1 | Growth Factors | −100 | −100 | −9.25 | Sprouty regulation of tyrosine kinase signals |
| CTGF | Growth Factors | 2 | −20 | 4 | Connective tissue growth factor, major connective tissue mitoattractant, Response to wounding, Proteinaceous extracellular matrix |

What can be deduced from table 5 is that with prolonged culture time, the expression level of genes involved in three dimensional arrangement and tissue formation is approaching the expression level observed in native dermal papilla fibroblasts.

TABLE 1

DMEM +− Dulbecco's modified Eagle Medium - Composition (Gibco)

| COMPONENTS | Molecular Weight | Concentration (mg/L) | Molarity (mM) |
|---|---|---|---|
| Amino Acids | | | |
| Glycine | 75 | 37.5 | 0.500 |
| L-Alanine | | 8.9 | |
| L-Arginine hydrochloride | | 84 | |
| L-Asparagine | | 13.2 | |
| L-Aspartic acid | | 13.3 | |
| L-Cystine 2HCl | | 63 | |
| L-Glutamic Acid | | 14.7 | |
| L-Histidine hydrochloride-H2O | | 42 | |
| L-Isoleucine | | 105 | |
| L-Leucine | | 105 | |
| L-Lysine hydrochloride | | 146 | |
| L-Methionine | | 30 | |
| L-Phenylalanine | | 66 | |
| L-Proline | | 11.5 | |
| L-Serine | | 52.5 | |
| L-Threonine | | 95 | |
| L-Tryptophan | | 16 | |
| L-Tyrosine disodium salt dihydrate | | 104 | |
| L-Valine | | 94 | |
| Vitamins | | | |
| Ascorbic Acid phosphate | | 2.5 | |
| Choline chloride | | 4 | |
| D-Calcium pantothenate | 477 | 4 | 0.00839 |
| Folic Acid | 441 | 4 | 0.00907 |
| i-Inositol | | 7.2 | |
| Niacinamide | | 4 | |

TABLE 1-continued

DMEM +− Dulbecco's modified Eagle Medium - Composition (Gibco)

| COMPONENTS | Molecular Weight | Concentration (mg/L) | Molarity (mM) |
|---|---|---|---|
| Pyridoxine hydrochloride | | 4 | |
| Riboflavin | | 0.4 | |
| Thiamine hydrochloride | | 4 | |
| Inorganic Salts | | | |
| Calcium Chloride (CaCl2) (anhyd.) | 111 | 200 | 1.80 |
| Ferric Nitrate (Fe(NO3)3"9H2O) | | 0.1 | |
| Magnesium Sulfate (MgSO4) (anhyd.) | | 97.67 | |
| Potassium Chloride (KCl) | | 400 | |
| Sodium Bicarbonate (NaHCO3) | | 3700 | |
| Sodium Chloride (NaCl) | | 6400 | |
| Sodium Phosphate dibasic (Na2HPO4—H2O) | | 125 | |
| Proteins | | | |
| AlbuMAX ® II | | 400 | |
| Human Transferrin (Holo) | | 7.5 | |
| Insulin Recombinant Full Chain | | 10 | |
| Trace Elements | | | |
| Ammonium Metavanadate | | 0.0003 | |
| Cupric Sulfate | | 0.00125 | |
| Manganous Chloride | | 5 | |
| Sodium Selenite | | 0.005 | |
| Other Components | | | |
| D-Glucoss (Dextrose) | | 4500 | |
| Ethanolamine | | 1.9 | |
| Glutathione (reduced) | 307 | 1 | 0.00326 |
| Phenol Red | | 15 | |
| Sodium Pyruvate | | 110 | |
| Penicillin | | 100 u/ml | 100 μ/ml | |
| Streptomycin | | | |
| GlutaMAX ™ | | | |

The invention claimed is:

1. A method for producing de novo papillae comprising the steps of:
   (a) providing at least one dermal papilla (DP) from at least one mammal hair follicle,
   (b) isolating dermal hair papilla fibroblasts (DPFs) from the DP by mechanically fixing said DP at the surface of a cell culture vessel, whereby the basal lamina is perforated to allow said DPFs migrating out,
   (c) expanding the isolated DPFs in monolayer culture without collagen coating, wherein said DPFs are passaged at least once,
   (d) condensing the expanded DPFs into cell aggregates that exhibit the size and shape of the physiological DP in a non-adhesive culture vessel;
   (e) differentiating the cell aggregates produced in (d) in non-adhesive culture vessels in a cell concentration per vessel surface of 1,000 to 100,000 DPFs/cm$^2$, and
   (f) coating the cell aggregates produced in (e) with extracellular matrix proteins, thereby producing de novo papillae.

2. The method of claim 1, wherein the expanded DPFs are condensed for at least 48 h.

3. The method according to claim 2, wherein the expanded DPFs are condensed for 2 to 21 or 3 to 15 days.

4. The method according to claim 1, wherein in step (d) non-inductive DPFs are condensed.

5. The method of claim 1 wherein the extracellular matrix proteins are collagen IV, fibronectin and/or laminin.

* * * * *